United States Patent

Sankey et al.

[11] Patent Number: 5,914,303
[45] Date of Patent: Jun. 22, 1999

[54] PERCARBOXYLIC ACIDS

[75] Inventors: John Phillip Sankey, Warrington; Alun Pryce James, Liverpool, both of United Kingdom

[73] Assignee: Solvay Interox Limited, Warrington, United Kingdom

[21] Appl. No.: 08/647,914

[22] PCT Filed: Dec. 12, 1994

[86] PCT No.: PCT/GB94/02718

§ 371 Date: May 30, 1996

§ 102(e) Date: May 30, 1996

[87] PCT Pub. No.: WO95/16673

PCT Pub. Date: Jun. 22, 1995

[30] Foreign Application Priority Data

Dec. 14, 1993 [GB] United Kingdom ............... 9325558

[51] Int. Cl.⁶ ............... C07C 407/00; C07C 409/40; C11D 3/39
[52] U.S. Cl. ............... 510/310; 252/186.1; 252/186.26; 252/186.38; 252/186.42; 510/376; 510/490; 562/2; 562/4
[58] Field of Search ............... 562/2, 4; 252/186.1, 252/186.26, 186.38, 186.42; 510/310, 376, 490

[56] References Cited

U.S. PATENT DOCUMENTS 4,634,551 1/1987 Burns et al. ............... 252/102
5,503,765 4/1996 Schepers et al. ............... 252/95
5,672,295 9/1997 Gary et al. ............... 252/186.42

FOREIGN PATENT DOCUMENTS 564250 10/1993 European Pat. Off. .
WO 95/03276 2/1995 WIPO .

OTHER PUBLICATIONS

Gilbert et al., J. Org. Chem., vol. 27, pp. 1336–1341, 1972.

*Primary Examiner*—Richard L. Raymond
*Attorney, Agent, or Firm*—Larson & Taylor

[57] ABSTRACT

An aromatic peroxyacid which satisfies the general formula (1):

$$X-Ar-CO-NY-R(Z)-CO-OOH \qquad (1)$$

in which X represents hydrogen or a compatible substituent, R represents $-(CH_2)_n-$ in which n=2 or 3, and Y and Z each represent independently a substituent selected from hydrogen or an alkyl or aryl group or an aryl group substituted by a compatible substituent or alkaryl group provided that at least one of Y and Z is not hydrogen if n=3. The peroxyacid is an effective bleaching and disinfecting agent which has a long shelf life and good resistance to impact, pressure and thermal shocks, and is useful in bleaching, washing and disinfecting compositions.

19 Claims, No Drawings

PERCARBOXYLIC ACIDS

This application is a 371 of PCT/GB94/02718, filed Dec. 12, 1984.

The present invention relates to percarboxylic acids and more particularly to percarboxylic acids which contain within their structure an amido linkage, to the preparation of such percarboxylic acids and to their use in bleaching compositions and in washing compositions.

Organic percarboxylic acids, as a class, more strictly called peroxycarboxylic acids, and sometimes alternatively called organic peracids, are potentially very useful oxidising agents in the home as a result of their high electropotential which enables them to bleach very effectively a wide range of stains that mark domestic laundry or non-absorbent surfaces and very useful disinfectants or sanitizers on account of their biocidal activity against a broad spectrum of pathogenic micro-organisms. Self-evidently, some percarboxylic acids are more effective than others in such activities, but the relative efficacy of the percompounds though of crucial importance, is only one factor in determining the potential usefulness of such percompounds. A second important factor comprises the physico-chemical characteristics of the percarboxylic acids and specifically their sensitivity to impact, pressure or thermal shock and their propensity to decompose during storage, either by themselves or in contact with other components of washing or bleaching compositions. Variation in respect of both factors occurs as a direct result of what else is present in the percarboxylic acid molecule and the structural relationship of for example the miscellaneous substituents to the percarboxylic acid group and to each other.

It is very easy for the skilled person in this field to set out his criteria for a most acceptable peroxyacid, namely effective washing and bleaching performance whilst offering sufficient resistance to impact, pressure and thermal shocks and a long shelf-storage life, ie successful, safe and stable, but it is not at all easy to predict from the formula alone the extent to which at least some sub-classes of peroxyacid satisfy those criteria, despite the impression fostered by the presence of general formulae for peracids in many older patent specifications, eg U.S. Pat. No. 4,259,201 of HO—O—(CO)—R—Y which make no or little distinction between aliphatic and aromatic peroxyacids and the presence or absence of a wide range of substituents.

In U.S. Pat. No. 5,098,598 to Sankey et al, assigned to Interox Chemicals Limited, it is disclosed that there are significant differences in the properties of within the classes of peroxyacids that contain an aromatic moiety, an aliphatic moiety and an amido linking group and satisfy one of two general formulae R1—CO—N (R$^5$)—R$^2$—CO—OOH and R$^1$—N (R$^5$)—CO—R$^2$—CO—OOH given by M E Burns et al in U.S. Pat. No. 4,634,551, by M E Burns in U.S. Pat. No. 4,686,063, both assigned to The Procter & Gamble Company and also in EP-A-0 170 386 in the name of the same assignee. Such properties include variations in bleach effectiveness, resistance to shock and storage stability of the various peroxyacids. Sankcey et al were able to demonstrate that a number of the peroxyacids that satisfied one or other of the Burns formulae were either relatively ineffective as a bleach and/or exhibited poor resistance to shock and/or showed relatively poor storage stability, whereas certain other and closely related selections of peroxyacids that were still within the formula surprisingly met all three criteria.

Sankey et al further demonstrated that a similar change such as increasing chain length in an alkylene substituent was shown to result in different effects, depending on the remainder of the molecule, for example improving thermal stability for one sub-set of peroxyacids, but impairing thermal stability for a second subset. One conclusion that can be deduced from the results disclosed by Sankey et al is that in respect of compounds containing an aromatic moiety and an amidoperacid subtituent, it was necessary for the amido linkage to be oriented such that its nitrogen atom is attached directly to the aromatic nucleus in order for those compounds to enjoy an acceptable combination of properties.

It is an object of the present invention to define a further set of peroxyacid compounds containing both an amide link and an aromatic group which simultaneously offer acceptable bleaching/washing performance and acceptable physical properties.

According to the present invention there is provided an organic peroxyacid which satisfies the general formula (1):

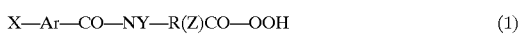

X—Ar—CO—NY—R(Z)CO—OOH     (1)

in which X represents hydrogen or a compatible substituent, R represents—(CH$_2$)$_n$— in which n=2 or 3, and Y and Z each represent independently a substituent selected from hydrogen or an alkyl or aryl or alkaryl group or an aryl group substituted by a compatible substituent provided that at least one of Y and Z is not hydrogen if n=3.

Surprisingly, and in contrast to the peroxyacids identified by Sankey et al, in the peroxyacids of the present invention, the aromatic nucleus is directly substituted by the carbonyl carbon in the amide linkage.

The substituent X on the benzene nucleus is often hydrogen and when it is not hydrogen it is advantageously meta or para to the amido-percarboxylic acid substituent. X can represent a halogen, typically chlorine atom, or some other non-released non-interfering species such as an alkyl group, conveniently up to C6 for example a methyl, ethyl or propyl group. Alternatively, X can represent a second amido-percarboxylic acid substituent of formula:

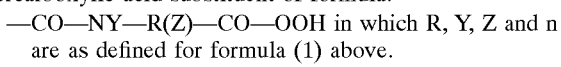

—CO—NY—R(Z)—CO—OOH in which R, Y, Z and n are as defined for formula (1) above.

Within the amido percarboxylic acid substituent, in a number of highly desirable embodiments, n=2 and both Y and Z are hydrogen.

In other desirable embodiments, one or other or even both of Y and Z is or are represented by a linear, branched, cyclic or substituted cyclic group which can be aliphatic or aromatic; including phenyl or substituted phenyl groups or benzyl or alkyl, eg C1–C4 group in the amido percarboxylic acid substituent. The alkyl group can in some desirable embodiments comprise cyclohexyl, and especially in respect of the Y group. The substituent of a cyclic group, if present, is typically a group that would not be released under manufacture of the peracid from the corresponding carboxylic acid, such as an alkyl or halo group. Most preferably the number of such Y plus Z groups in the amido percarboxylic acid substituent is either 1 or 2. Thus, in such latter preferred compounds, the alkylene moiety R is either linear bi or trimethylene or one or two of the methylene groups may be substituted, the number and location of the substitutions being at the discretion of the producer of the percarboxylic acid.

In certain other embodiments, where n=3 in the formula for R, either Y and/or Z represents a non-hydrogen substituent, and particularly represents a phenyl or substituted phenyl or benzyl group. By so substituting R and/or the amido nitrogen the resultant peracid can combine the advantageous washing properties of products in which n=3 with the added safety and stability arising from the substitution.

A number of suitable amidoperacids according to the present invention comprise benzoyl-amido-3-ethyl-perpropionic acid, benzoyl-amido-3-cyclohexyl-perpropionic acid, N-phenyl-benzoyl-amido-3-ethyl-perpropionic acid, N-benzyl-benzoyl-amido-3-ethyl-perpropionic acid, benzoyl-amido-3-methylperpropionic acid, N-phenyl-benzoyl-amido-3-methyl-perpropionic acid, N-benzyl-benzoyl-amido-3-methyl-perpropionic acid, N-phenyl-benzoyl-amido-perpropionic acid, N-benzyl-benzoyl-amido-perpropionic acid, N-cyclohexyl-benzoyl-amido-perpropionic acid, N-phenyl-benzoyl-amido-perbutanoic acid, N-benzyl-benzoyl-amido-perbutanoic acid, N-cyclohexyl-benzoyl-amido-perbutanoic acid, N-methyl-benzoyl-amido-3-phenyl-perpropionic acid, N-ethyl-benzoyl-amido-3-phenyl-perpropionic acid and N-cyclohexyl-benzoyl-amido-3-phenyl-perpropionic acid.

The peroxyacids of the present invention can be made using a strong acid-catalysed reaction between hydrogen peroxide and the corresponding compound containing a carboxylic acid group in the same structural relationship to the amido group as is desired in the peroxycarboxylic acid compound, of formula (2:

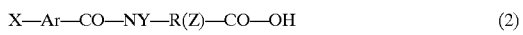

(2)

in which R, X, Y and Z have the same definitions as in formula (1) and preferably employing conditions that have hitherto been described for the peroxidation of other aromatic carboxylic acids or preparation of poorly soluble higher molecular weight aliphatic peroxyacids from their corresponding carboxylic acid. In effect, the teaching in such prior publications as Siegel, et al in JOC, vol 27 pp1336–42 in 1961 entitled peroxides IX. New Method for the Direct Preparation of Aromatic and Aliphatic Peroxyacids and U.S. Pat. No. 5,098,598 can be employed, but modified as to the carboxylic acid starting materials.

In some suitabe preparative processes, the reaction medium for the peroxidation reaction is especially suitably an organic sulphonic acid, such as specifically methane sulphonic acid, which is probably the most readily available lower alcane sulphonic acid. In other suitable processes all or a proportion of the organic sulphonic acid can be replaced by a strong inorganic acid, such as especially sulphuric acid. It will be understood that where hydrogen peroxide and a strong acid, particularly sulphuric acid are employed in conjunction with each other to carry out the peroxidation reaction, all or part of them can be premixed with each other to form an equilibrium mixture containing for example permonosulphuric acid that can itself perform the peroxidation reaction. Such premixing is beneficial because it separates the exothermic dilution/reaction between hydrogen peroxide and sulphuric acid from the peroxidation reaction, thereby enabling both to be controlled more readily and safely.

The attention of readers not skilled in the art of peroxygen chemistry is directed to the potentially hazardous nature of peroxidation reactions and their products, to the need to take appropriate safety precautions at all times and to monitor and control the reaction conditions so as to ensure that the temperature of the reaction mixture is either below its SADT, self accelerating decomposition temperature or at least never increases at an uncontrollable rate, and to carry out any initial tests on a very small scale.

Notwithstanding the above general warning which is of particular relevance to many other peroxyacids, the peroxyacids of the instant invention are characterised by their generally benign properties, specifically their relatively high stability and resistance to decomposition which they combine with acceptable bleach performance.

The amido-containing carboxylic acids, if they are not readily available, can themselves be obtained by a Schotten Baumann reaction between the appropriate benzoyl chloride and the appropriate aminoalkylenecarboxylic acid.

Whilst the instant invention relates primarily to the peroxyacids themselves, it will be understood that it is possible to form magnesium salt derivatives of the peroxyacids by neutralisation using magnesium oxide or similar compounds in media rendered alkaline to above the pKa of the peroxyacid and recovery of the product that is permitted or induced to precipitate out. These corresponding salts share the stability and performance of the peroxyacids themselves, and accordingly could be employed. However, it will be recognised that it is of benefit for washing and bleaching purposes to avoid the un-necessary introduction of cations that directly contribute to water-hardness, such as magnesium. This particular benefit is inherent in the use of the instant selection of peroxyacids, but is not retained when the corresponding magnesium salt is used. Such magnesium salts tend to enjoy a markedly higher solubility and rate of dissolution than the acid form from which they are derived. Thus, it will be immediately recognised that where it is beneficial to employ a peroxyacid having high water solubility, the user can employ the magnesium salt form of the invention peroxyacids. Where it is desirable to employ peroxyacids having relatively low water solubility, so as to minimise or eliminate bleach spotting problems, the acid form of the invention peroxyacids can be used.

The percarboxylic acids according to the instant invention are particulate solids and they can be employed by themselves or can be incorporated as an active bleach component in bleaching or washing compositions containing a range of other ingredients, the selection and amounts of which are at the discretion of the formulator and determine the name for the compositions.

For bleach or bleach additive compositions, the peroxyacid normally comprises from 1 to 80%, and often from 5 to 50%, all %s herein being w/w of the respective composition unless otherwise stated. The remainder, 99 to 20%, comprises a diluent either by itself or together with a minor amount, such as up to 20% in total of optional components such as peroxygen stabilisers, surfactants, etc as indicated subsequently herein. The skilled reader will recognise that many of the diluents described herein as being suitable have hitherto been described as one or other of desensitising diluents or stabilising diluents or exotherm control agents in conjunction with named prior art organic peroxyacids such as diperoxyphthalic acid or DPDDA. Whilst the presence of such diluent compounds may have been necessary to perform that function for those prior art peroxyacids, it is a significant feature of most of the invention peroxyacids that the presence of the same diluents is optional rather than essential and in practice their selection can be based upon any other desirable feature of those diluent compounds, such as their cheapness or their advantageous washing or detergent-enhancing properties. The diluent is often a salt selected from anhydrous or hydrated alkali or alkaline earth metal salts of halogen-free acids, and particularly of mineral acids, including salts of sulphuric, and ortho, pyro or hexameta phosphoric acids. Preferably, the metal is selected from sodium, potassium and magnesium and in many instances is sodium. Hydrated, partially hydrated or anhydrous sodium sulphate is often chosen in view of its widespread availability, its properties and its cost. It will be recognised, though, that use of a phosphate salt may be preferred in view of its known capabilities of acting as a detergent builder, which can complement especially an unbuilt washing composition.

Other inorganic compounds that are suitable for use as diluents include ortho and meta boric acid and alkali metal salts thereof, and especially sodium salts. Such compounds can buffer solutions of the bleach or additive composition to a pH in the immediate region of the pKa of the peroxyacid and consequently optimise bleach activity. The boric acids have also been used as exotherm control agents in compositions containing peroxyacids such as DPDDA that need to be protected against a tendency to decompose in an otherwise uncontrollable fashion if allowed to reach a quite low threshold temperature, but that property is unnecessary in conjunction with the invention peroxyacids on account of the safe nature of these selected amidoaryl peroxyacids.

Other suitable inorganic diluents include alkali metal carbonates/bicarbonates, aluminium salts of the above-identified mineral acids, and natural or synthetic aluminosilicates and clays, such as zeolites A, X Y, and MAP, often in the sodium form, or swelling clays like bentonite. It will be clearly recognised that many of these diluents also enjoy the status of builders in washing compositions, and that each accordingly can perform its known functions such as hardness removal or peptising when employed in bleach compositions. When the bleach composition is intended as a scour, at least a proportion of the diluent and preferably at least half of the diluent comprises abrasive powdered materials, including silica, quartz, marble dust or kieselguhr.

A further and rather different class of suitable inorganic diluents comprises alkai metal or alkaline earth metal halides, especially chlorides and/or bromides and particularly sodium chloride, or sodium bromide or a mixture of the two. By employing this class of diluents as at least a part of the diluents, the composition can generate in solution during use of the composition a halide such as chlorine or bromine which can complement the bleaching/sanitising effect of the invention amidoaryl peroxyacids.

The diluent can comprise a hydrogen peroxide—developing solid persalts, or an inorganic persulphate, preferably in an amount of not more than 50% w/w of the composition. The term "persalt" herein relates primarily to alkali metal perborates, percarbonates and perphosphates, and especially the sodium salts, which generate hydrogen peroxide or the HOO-anion depending on the solution pH, in situ and includes other hydrogen peroxide adducts which can do likewise. Preferred persalts include sodium perborate monohydrate or tetrahydrate and sodium percarbonate. Persalts include adducts with urea and related compounds, adducts with certain aluminosilicates and addition compounds with allkali/allkaline earth metal sulphate/chlorides-in specified ratios. It will be recognised that the use of persalts as diluent, such as in at least 10% of the composition, enables the composition to be effective throughout a range of temperatures from ambient up to about 100° C.

In one more specialised type of bleaching compositions, namely effervescent composition, which are often intended primarily for cleansing dentures, but which can also be employed for many other purposes, the diluent for the invention peroxyacids preferably contains a gas generating system and if necessary a pH regulator. Compounds that are suitable for gas generating systems and as pH regulators are well known in conjunction with existing peroxyacids, and are described in EP-A-0 133 354 in the name of Interox Chemicals Limited. The gas generating system often provides from 10 to 50% and comprises either a carbon dioxide generating combination of an alkali metal carbonate or bicarbonate with a solid water-soluble acid, and especially an organic acid selected from tartaric, citric, lactic, succinic, glutaric, maleic, fumaric and malonic acids, preferably in an equivalent mole ratio of from 1.5:1 to 1:1.5 and especially at about 1:1, or an oxygen-generating compound such as anhydrous sodium perborate. The pH regulator often comprises 5 to 40% of the composition. To provide acidic conditions, it can comprise one or more of the aforementioned organic acids in an appropriate excess amount, or sulphamic acid or alkali metal bisulphates, and to provide alkaline conditions, it can comprise alkali metal silicates or excess carbonate/bicarbonates. Selection of the percarboxylic salt form can be advantageous in such compositions.

In the main, the foregoing diluents have been inorganic. However, the invention peroxyacids can be diluted, if desired, with a range of organic substances, including hydrocarbon waxes, alkyl C1 to C6 esters of aromatic mono or di carboxylic acids, solid starches, gelatines and dextrins.

The bleach compositions can also contain, as indicated before, in minor amounts, components such as peroxyacid stabilisers. The breadth of compounds suitable for this purpose is well-known in this art. These are often organic chelating compounds that sequester metal ions in solution, particularly most transition metal ions, which would promote decomposition of any peroxygen compounds therein, and many suitable ones being classified in the literature as carboxylic acid, hydroxycarboxylic or aminocarboxylic acid complexing agents or as organic amino- or hydroxy-polyphosphonic acid complexing agents, either in acid or soluble salt forms. Representative stabilisers expressed in acid form include picolinic acid, dipicolinic acid, quinolinic acid, gluconic acid, hydroxyethylene di phosphonic acid, and any compound satisfying the general formula:

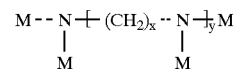

in which M represents either —$CH_2$—$CO_2H$ or —$CH_2$—$PO_3H_2$, x represents an integer selected from 1 to 6, and preferably is 2, and y represents an integer selected from 0, 1, 2 or 3. Within this general formula especially preferred stabilisers include ethylenediamine tetra acetic acid (EDTA), ethylenediamine tetrakis (methylenephosphonic acid) (EDTMP), and diethylenetriamine pentakis (methylenephosphonic acid) (DTPMP). An alternative and highly effective stabiliser comprises cyclohexane-1,2-tetramethylene phosphonic acid. The amount of stabiliser is often up to 5% of the composition and in many instances is selected in the range of from 0.05 to 1%.

If present at all, a surfactant is present in bleaching compositions only in a small amount, such as up to about 5% and in many instances from 0.1 to 2% of the composition. It can be selected from the surfactants described subsequently herein for washing compositions.

The invention bleaching compositions will often comprise particulate mixtures, which can be stored loosely in conventional waxed boxes, or alternatively enclosed in rupturable pouches or in porous or perforated bags or sacs through which bleaching solution can penetrate. Such mixtures can be obtained by dry blending the particulate components, or they can be aggregated using conventional agglomeration or granulation techniques, using water or a removable solvent and optionally a granulating aid hitherto described for use with an organic peroxyacid. Alternatively, by virtue of their demonstrated ability to withstand pressure, all but the least resistant invention peroxyacids can be compressed in tablets and like bodies. Accordingly, it is possible to provide peroxyacids in easy to use predetermined dosage levels for the end user.

The bleaching compositions can be used by themselves, such as in a pre-wash bleach or a post-wash rinsing stage of a multistage laundry process or in cleansing both absorbent or non-absorbent (sometimes called "hard") surfaces. They are more usually employed in conjunction with a washing composition based upon surfactants. Naturally, surfactants and optional ingredients of washing compositions can be premixed with the instant bleaching compositions to form bleach-containing washing compositions.

Washing compositions according to this further aspect of the present invention contain from 0.5 to 50% of the invention amidoaryl peroxyacids, from 1 to 90% surfactant, from 0 to 90% detergent builder, from 0 to 90% diluent and from 0 to 20% minor components. It will be recognised that the composition of the invention washing compositions range within very broad limits. Choice of the peroxyacid in acid form can be beneficial herein, in order to minimise or avoid spotting problems that can occur if excessive local concentrations of active bleach should be allowed to remain in contact with a dyed fabric for too long.

In many preferred compositions according to the present invention, one or more of the composition components are selected within the following narrower bands:

| | |
|---|---|
| amido peroxyacid | 1 to 25%, particularly 2 to 10% |
| surfactant | 2 to 40%, particularly 5 to 25% |
| builder | 1 to 60%, particularly 5 to 40% |
| diluent | 1 to 70%, particularly 5 to 50% |
| minor components | 1 to 10% in total. |

The surfactants for incorporation in solid compositions of the present invention can be selected from particulate or flaky anionic, cationic, non-ionic, zwitterionic, amphoteric and ampholytic surfactants and can be either natural soaps or synthetic. A number of suitable surfactants are described in chapter 2 of Synthetic Detergents by A Davidsohn and B M Milwidsky (6th edition) published in 1978 by George Godwin Ltd and John Wiley & Sons, incorporated herein by reference.

Without limiting to the above mentioned surfactants, representative sub-classes of anionic surfactants are carboxylic acid soaps, alkyl aryl sulphonates, olefin sulphonates, linear alkane sulphonates, hydroxy-alkane sulphonates, long chain and OXO alcohol sulphates, sulphated glycerides, sulphated ethers, sulpho-succinates, alkane sulphonates, phosphate esters, sucrose esters and anionic fluorosurfactants; representative classes of cationic surfactants include quaternary ammonium or quaternary pyridinium salts containing at least one hydrophobic alkyl or aralkyl group, representative classes of nonionic surfactants include condensates of a long chain alkanol with either polyethylene oxides or with phenols, or condensates of long chain carboxylic acids or amines or amides with polyethylene oxide, and related compounds in which the long chain moiety is condensed with an aliphatic polypol such as sorbitol or condensation products of ethylene and propylene oxides or fatty acid alkanolamides and fatty acid amine oxides; representative classes of amphoteric/zwitterionic surfactants include sulphonium and phophonium surfactants, optionally substituted by an anionic solubilising group. The proportion of surfactant, expressed as a fraction of all the surfactant present is often from $2/10$ to $8/10$ths anionic, from 0 to $6/10$ths nonionic, and from 0 to $3/10$ths for the other surfactants.

It will be recognised by the knowledgable reader that many of the classes of diluent described herein above for use in bleaching compositions are also called detergent builders. These include specifically alkali metal phosphates, particularly tripolyphosphate but also tetrapyrophosphate and hexametaphosphate, especially the sodium salt of each, alkali metal, preferably, sodium carbonate, alkali metal, preferably, sodium borates, and the zeolites A, X, Y and MAP, layered silicates as in a product available under the mark SKS6 and clays like bentonite. Amongst organic compounds, the chelating compounds which were described herein as peroxygen stabilisers can also function as detergent builders. Particularly preferred chelating builders include nitrilotrisodium trisacetate (NTA), EDTA, EDTMP and DTPMP. Such chelating builders can be employed in a relatively small amount as an augmenting builder and peroxygen stabiliser, such as of 1 to 10%, or in cooperative partnership of equals in conjunction with a phosphatic or zeolitic or clay builder, the weight ratio of chelating to inorganic builders often being from 4:1 to 1:4, or alternatively they can be employed as the principal builder in amounts of up to 40% such as in the range of 5 to 30% of the washing composition.

The other types of compounds that have been indicated to be suitable for use as diluents in a bleaching composition, can also be employed for the same primary purpose and secondary purpose, if any, in washing compositions, although it will be recognised that the presence of an effervescent system in washing compositions is comparatively rare. For the avoidance of doubt, persalts can be incorporated in the instant washing compositions, preferably in an amount of up to 30%, such as 1 to 20%, and sometimes in a weight ratio to the invention amidoaryl peroxyacids of from 5:1 to 1:5. A diluent commonly present in these washing compositions is sodium sulphate, often from 5 to 50%, because it also functions as a processing aid. The previously mentioned salts that enable a halogen to be generated in situ can likewise be present in the washing compositions, which can then enjoy the alternative name of sanitising compositions.

The washing compositions can contain a number of optional components, sometimes alternatively called auxiliary agents. These agents which can each individually be included include soil anti redeposition agents (SARDs), dye transfer inhibitors, optical brightening agents (OBAs), stabilisers, corrosion inhibitors, bactericides, dyes, perfumes, foam enhancers, foam inhibitors, pH regulators and absorbents. The amount for each auxiliary agent is often selected in the range of 0.02 to 0.2% for dyes and perfumes and from 0.1 to 2% for each of the other auxiliary agents. It is preferable to select auxiliary agents which are known not to interact with peroxygen compounds during storage or to coat the agent with or incorporate the agent in a known fashion within a matrix of a dispersible material such as a wax or the many other film-forming substances proposed in the literature for separating organic peroxygen compounds from co-components, eg in EP-B-00 27 693 to Interox Chemicals Limited. Such substances can also function as granulating aids (binders), if the invention compositions are granulated or agglomerated. Examples of suitable SARDs include carboxymethyl cellulose particularly the sodium salt, polyvinylpyrrolidone and examples of OBAs include derivatives of diaminostilbene sulphonic acid and 1,3-diaryl-2-pyrazolines and aminocoumarins and OBAs described in EP-A-0 548 019.

The invention washing compositions can be dampened or dissolved in a little water for cleaning and disinfecting non-adsorbent surfaces such as walls, floors, work surfaces, vessels, baths, sinks and sanitaryware of metal, plastics, ceramics or glass, wood and rubber.

One of the main intended uses of the washing compositions is to cleanse and indeed also disinfect soiled adsorbent materials such as household laundry items or other articles made especially from cotton, rayon, flax or wool or man-made fibres such as polyesters or polyamides. The cleansing processes can be carried out at ambient temperature or at elevated temperature up to the boiling temperature of the washing solution. The more preferred washing temperature for laundry is from 30 to 60° C. In laundering, it is desirable to introduce sufficient washing composition and/or bleach additive composition to provide at least 5 ppm avox from the amidoaryl peroxyacid, and often from 10 to 50 ppm avox, ppm indicating parts per million by weight and avox indicating available oxygen. This can often be provided by the introduction of the invention washing composition selected in the range of 1 to 25 gpl, or bleach additive composition selected in the range of from 0.5 to 10 gpl, the selection taking into account the concentration of amidoaryl peroxyacid therein. The presence of persalts in the wash can supplement avox levels, for example by amounts of from 10 to 100 ppm avox. In use, depending upon whether and the extent to which alkaline materials, especially builders, are present in the composition itself or in any accompanying washing composition, the compositions generate upon dissolution either a mildly acidic through to especially a mildly alkaline pH. It is preferred to generate a pH of from 7.5 to 9.5 and especially around pH of 8 to about 9.0 to optimise bleaching/washing performance from the peroxyacid.

For use in disinfection, it is often preferable to employ an invention peroxyacid concentration of up to 200 ppm avox and in many instances from 25 to 100 ppm avox. It is also suitable to employ a solution spanning neutrality, from mildly acidic, such as at least pH 4 up to mildly alkaline, such as pH 9. In order to attain a pH in such a range, the choice of builders/diluents is so made as to avoid highly alkaline materials and instead select those that generate mild acidity or alkaninity such as sodium dihydrogen phosphate.

The washing processes for laundry can be carried out in currently available equipment. Washing times typically range from about 10 minutes to 30 minutes. Hand washing and extended steeping using solutions of the invention compositions can alternatively or additionally be used. Specialist variations of the invention compositions, such as those intended for nappy sanitisation/cleansing or for denture cleansing are preferably used in the accepted manner for prior art compositions, for example steeping a soiled nappy in a warm peracid-containing solution for several hours before washing it using laundry techniques.

Having described the invention in general terms, specific embodiments will now be described more fully by way of example only.

EXAMPLE 1

Preparation of 3-Benzoyl-amido perpropanoic acid.

In this Example, the reaction equation for the acid catalysed reaction was:

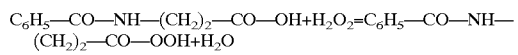

The general preparative route adopted for the first preparation of the peroxyacid was as follows:

The benzoyl amido carboxylic acid (10 g) was introduced into stirred methanesulphonic acid (40 mls) in a beaker, forming a solution or suspension depending upon the solubility of the reactant, and the mixture was cooled to 5° C. in a water/ice bath. Hydrogen peroxide assaying 85% w/w approx. aqueous solution, was pumped via a peristaltic pump with continued stirring into the reaction mixture progressively during a period of about 5 to 10 minutes at a rate controlled so that the mixture's temperature did not rise above 5° C., until a total amount of 4 moles per mole of carboxylic acid had been introduced, ie a 3 molar excess compared with the stoichiometric amount. During the subsequent 90 minutes, the reaction mixture was permitted to warm to ambient temperature, ie about 20° C. whilst still being stirred. By the end of the reaction a substantial fraction of the carboxylic acid had been oxidised to the corresponding peroxycarboxylic acid, which precipitated out of solution to an extent that varied according to the particular peroxyacid.

The precipitated product was recovered from the reaction mixture by pouring the reaction mixture was poured into about 3 times its volume of iced water, filtered and the filter cake washed twice with about 30 to 40 mls of cool water each time and finally air-dried.

The isolated peroxyacid product was then analysed by conventional IR techniques to confirm the presence of amido and percarboxylic acid groups in the product molecule, its available oxygen content measured, again to confirm the presence of a peroxygen species and its "melting" point measured.

The Avox % figure given in Tables 1 and 2, is the percentage obtained by comparing the proportion of peracid avox (available oxygen) measured in the product with the theoretical avox calculated from the molecular formula (16/molecular weight) of the intended peroxycarboxylic acid. The avox was measured by a standard technique in which a measured weight of sample was dissolvet in acetic acid, if necessary augmented with dichloromethane to ensure that the sample is completely dissolved. The sample is then contacted with a measured amount of sodium carbonate stabilised sodium iodide, in the presence of ferric chloride, allowed to react for 10 minutes in the dark, and the resultant solution is titrated against standardised sodium thiosulphate solution until the pale yellow coloured solution becomes colourless. The result is compared with a corresponding titration against a blank solution, and from the difference the avox is calculated.

The product of Example 1,3-benzoyl amido perpropanoic acid was obtained in a yield of approximately 90% having an avox of 7.43% ie a purity of about 97%. Its melting point was 115° C.

For the product of Ex 1, three significant infra-red peaks were identified. The first was centred on 3250 cm−1, and this is indicative of N—H stretching in CO—N—H. The second peakl was centred on 1775 cm−1, indicative of carbonyl stretching in a peroxycarboxylic acid which is a substituent of an alkylene chain and there was a third peak, centred on 1625 cm−1, which characterise carbonyl stretching in —CO—NH—. By noting the similarities and the extent of the differences in the infra red data compared with the substrate carboxylic acid, it can be recognised that the peracid retained its amide group and that the carboxylic acid group was oxidised to a peroxycarboxylic acid group. The structure was confirmed by X ray crystallographic data.

EXAMPLE 2

In this Example, a solution of Caro's acid was prepared by mixing sulphuric acid (98% w/w, 20.4 g) and hydrogen peroxide solution (85% w/w, 6.3 g) and demineralised water (5.3 g) with cooling to 20° C., thereby obtaining an equilibrium mixture. 3-benzoyl amido propanoic acid (10 g) was then introduced, resulting after 10 minutes stirring in a thick white slurry which was stirred, still at ambient temperature, for a further 90 minutes. The reaction mixture was then quenched with ice (100 g), and filtered. The white precipitate was washed with cold water (3×100 ml) allowed to dry and then analysed. The yield of product was 54% based on the 3-benzoyl amido propanoic acid added, having a purity, determined by avox of 91.8%.

The process of Example 1 was repeated, but using the corresponding carboxylic substrates to prepare 2-Benzoyl-amido peracetic acid called CA herein, 5-benzoyl-amido-perpentanoic acid called CB, and the corresponding peracid to Ex1 in which the amido linkage is reversed (ie of formula $C_6H_5$—NH—CO—$CH_2$—$CH_2$—$CO_3H$) called CC.

Testing of the Peroxyacids

The peroxyacid of Ex 1 and its comparison peracids CA,CB and CC were subjected to a number of tests to determine the hazard rating and storage stability of each, and if satisfactory, their effectiveness as a bleach was also tested. The compounds were also compared in these tests with a reference peroxyacid, diperoxydodecanedioc acid, DPDDA, a peroxyacid that has emerged during the last eight years as a favourite organic peroxide amongst washing composition manufacturers.

The tests were carried out as follows:

Storage Stability

In this test, weighed samples of the peroxyacid are individually sealed in glass phials with a bubbler cap that permits excess internal pressure to vent to atmosphere, and stored in a dark chamber that is thermostatically controlled to 32° C. The Avox of the peroxyacid is measured shortly after its preparation ie AO and after predetermined storage intervals, the measurement being made on entire individual samples. The stability results of stored samples (As) are compared with the original measurement to generate the fraction As/AO, the Avox remaining,which is quoted in Table 1 as a percentage.

Avox is measured using the same method as described previously herein.

It will be recognised that the storage stability of the peroxyacid by itself is one of its extremely important characteristics, not only because the compound is likely to be stored in by itself before it is encorporated in specific compositions, but also because represents its intrinsic stability, the maximum attainable even if the remaining components of compositions containing it are benign.

TABLE 1

| Peracid Tested | Rate of Avox loss |
| --- | --- |
| 3-benzoyl amido perpropanoic acid | 16% in 16 weeks |
| CA | not measured |
| CB | 25% in 1 day |
| CC | 81% in 4 weeks |
| DPDDA | 15% in 4 weeks. |

From Table 1, it can be seen that neither of the comparisons CB nor CC had acceptable storage stability, DPDDA had an intermediate stability that was still 4 times worse than the product of Example 1 which showed excellent stability.

In the impact sensitivity test, a weight (in kg) is dropped once from a measured height (in cm) onto a fresh sample of the peroxyacid held in the anvil. The sample is thus subjected to an impact, normally expressed as kg-cm (1 kg-cm= $9.8×10^{-2}$J) that is proportionate to the height and weight. The test is carried out many times at each impact strength, and is observed to see whether the sample responds, by charring, emitting smoke or at worst undergoing a minor explosion. The tests start at a low impact strength and are continued at increasing strenghts until the limiting result is obtained, being the earlier of either 50% of the tests at that impact strength give positive results or a figure of 500 kg-cm is reached, which past experience indicates to represent a non-impact-sensitive product. The limiting result in kg-cm is shown in Tables summarising the results, the higher the better.

In the pressure-time test, 2 g samples of the test material is placed inside an 18 ml steel bomb, and its decomposition initiated. The consequential rise in pressure is monitored and plotted or displayed against elapsed time, expressed in milliseconds. In Table 2, the time is given for the pressure in the bomb generated by the sample to increase from 100 to 300 psi, ie from $6.895×10^5$ Pa to $2.068×10^6$ Pa, the longer the time, the safer is the test material. By way of interpretation, a time of less than 30 milliseconds indicates that the material is potentially explosive, a time of 30 to 60 milliseconds indicates that it is marginally explosive, and to allow a safety margin, it is preferred to be around 100 milliseconds or longer.

TABLE 2

| Peracid tested | Impact test | Pressure test |
| --- | --- | --- |
| 3-benzoyl perpropanoic acid | >500 Kg-cm | 180 ms |
| CA | 150 Kg-cm | |
| CB | liquid | |
| CC | 350 Kg-cm | 130 ms |
| DPDDA | >500 kg-cm | 30 ms |

From Table 2, it can be seen the comparison peracid CA had a poor resistance to impact and a rapid response in the pressure test indicating that it was relatively unacceptable for use in domestic formulations, whereas the closely related 3-benzoyl perpropanoic acid was appropriately resistant to impact and gave a much slower response time in the pressure test, which, following only minor dilution by resulted in an infinite response time confirming its safety.

From the foregoing Tables, it can be seen that none of the comparison amido peracids CA, CB, nor CC passed both the tests of safety and stability whereas the closely related invention peracid did indeed pass both such tests.

The effectiveness of the invention peroxyacid was tested by washing swatches of cotton cloth that had been pre-impregnated in a standard manner with one of four representative stains, tea, red wine, grass and blue polish. The evaluations were carried out in a laboratory scale washing machine, a "Tergotometer" (Trade Mark) available from the US Testing Corporation, under identical standardised conditions. The washing solution comprised local Cheshire tap water, hardness of about 160 to 180 ppm hardness as calcium carbonate, in which was dissolved a peroxyacid-free washing composition at 6.5 g/l. The composition was a particulate heavy duty base washing composition which was free of peracid and on analysis was found to contain about 23% w/w zeolite 4A as builder and about 25% sulphate diluent.

A weighed amount of peroxyacid was introduced into the washing solution to provide a peracid avox of 25 ppm therein on total dissolution. This corresponds to a molar concentration of $1.56×10^{-3}$M monoperoxyacid. The washing solution was kept at pH9 and at 40° C. during the washing period of 20 minutes. The swatches were then rinsed and dried and the extent of stain removal was determined by comparing the reflectance of the washed cloth, Rw, with that of the pre-washed, stained cloth, Rs, and that of the unstained cloth, Ru. The measurements were obtained using an Instrumental Colour System "Micromatch" (Trade Mark) reflectance spectrophotomer equipped with a Xenon lamp filtered through a D65 conversion filter to approximate to CIE artificial daylight. Stain Removal, expressed as a percentage, was calculated using the formula: %SR=100× [Rw−Rs]/[Ru−Rs]. It will be recognised that by demonstrating the washing capability of the peroxyacid in this way, the tests using the invention peroxyacid are in themselves Examples of washing processes according to other aspects of the present invention. Similarly, since the swatches had not been stored in sterile conditions before being washed, the washing procedure will act simultaneously to disinfect them.

The results quoted below are the mean of two evaluations. Comparative results on the same stained cloths using the washing composition by itself, ie without any added peracid, are designated "base".

TABLE 3

| Washing employed | % Stain Removal from | | | |
|---|---|---|---|---|
| | Red Wine | Grass | Tea | Blue Polish |
| Base | 43 | 48 | 66 | 37 |
| Base + Ex 1 peracid | 68 | 66 | 82 | 45 |
| Base + DPDDA | 63 | 66 | 81 | 44 |

From Table 3, it can be seen that the invention peracid was always at least as effective at stain removal as the reference peracid DPDDA in the washing trials, and on average removed almost 2% more stain.

We claim:

1. An organic peroxyacid which satisfies the general formula (1):

$$X—C_6H_4—CO—NY—R(Z)—CO—OOH \qquad (1)$$

in which X represents hydrogen, halogen or a alkyl group, R represents $—(CH_2)_n—$ in which n=2 or 3, and Y and Z each represent independently a substituent selected from hydrogen, aryl or alkaryl group provided that at least one of Y and Z is not hydrogen if n=3.

2. A peroxyacid according to claim 1 wherein Y and Z each represent hydrogen and n=2.

3. A peroxyacid according to claim 2 wherein X represents hydrogen.

4. A peracid according to claim 1 wherein one only of Y and Z represents a phenyl or substituted phenyl or benzyl or cyclohexyl group.

5. A process for the production of an organic peroxyacid of formula (1):

$$X—C_6H_4—CO—NY—R(Z)—CO—OOH \qquad (1)$$

in which X represents hydrogen, halogen, or an alkyl group, R represents $—(CH_2)_n—$ in which n=2 or 3, and Y and Z each represent independently a substituent selected from hydrogen, aryl, or alkaryl group provided that at least one of Y and Z is not hydrogen if n=3;

which comprises reacting an organic carboxylic acid of formula (2):

$$X—C_6H_4—CO—NY—R(Z)—CO—OH \qquad (2)$$

in which R, X, Y, Z have the same definitions as in formula (1) with excess aqueous hydrogen peroxide in a strong acid medium selected from organic sulphonic acids and sulphuric acid at reaction temperature of from about −5 to 50° C. until at least some peroxyacid product has been produced as a solid, and thereafter recovering the solid product from the reaction mixture.

6. A process according to claim 5 wherein the organic sulphonic acid reaction medium comprises methane sulphonic acid.

7. A process according to claim 5 wherein sulphuric acid is employed as a premixture with the hydrogen peroxide reactant.

8. A bleach composition containing from 1 to 80% w/w of an organic peroxyacid which satisfies general formula (1):

$$X—C_6H_4—CO—NY—R(Z)—CO—OOH \qquad (1)$$

in which X represents hydrogen, halogen, or an alkyl group, R represents $—(CH_2)_n—$ in which n=2 or 3, and Y and Z each represent independently a substituent selected from hydrogen, aryl or alkaryl group provided that at least one of Y and Z is not hydrogen if n=3 and from 99 to 20% w/w of a diluent.

9. A washing composition containing from 0.5 to 50% w/w of an organic peroxyacid which satisfies the general formula (1):

$$X—C_6H_4—CO—NY—R(Z)—CO—OOH \qquad (1)$$

in which X represents hydrogen, halogen, or an alkyl group, R represents $—(CH_2)_n—$ in which n=2 or 3, and Y and Z each represent independently a substituent selected from hydrogen or an alkyl aryl, or alkaryl group provided that at least one of Y and Z is not hydrogen if n=3 from 1 to 90% surfactant, from 0 to 90% detergent builder, from 0 to 90% diluent and from 0 to 20% minor components.

10. In a method of bleaching or disinfecting an article which comprises contacting an article with an organic peroxyacid to bleach or disinfect the article, the improvement wherein the organic peroxyacid satisfies the general formula (1):

$$X—C_6H_4—CO—NY—R(Z)—CO—OOH \qquad (1)$$

in which X represents hydrogen, halogen, or an alkyl group, R represents $—(CH_2)_n—$ in which n=2 or 3, and Y and Z each represent independently a substituent selected from hydrogen or an alkyl, aryl or alkaryl group provided that at least one of Y and Z is not hydrogen if n=3.

11. A method according to claim 10 wherein Y and Z each represent hydrogen, and n=2.

12. A method according to claim 11 wherein X, represents hydrogen.

13. A method according to claim 10 wherein one only of Y and Z represents a phenol or substituted phenyl or benzyl or cyclohexyl group.

14. A method according to claim 10 wherein the organic peroxyacid is present in a bleach composition containing from 1 to 80% w/w of the organic peroxyacid, and from 99 to 20% w/w of a diluent.

15. In a method of washing an article which comprises washing an article with a composition which includes an organic peroxyacid, the improvement wherein the organic peroxyacid satisfies the general formula (1):

$$X-C_6H_4-CO-NY-R(Z)-CO-OOH \qquad (1)$$

in which X represents hydrogen, halogen, or an alkyl group, R represents $-(CH_2)_n-$ in which n=2 or 3, and Y and Z each represent independently a substituent selected from hydrogen or an alkyl, aryl or alkaryl group provided that at least one of Y and Z is not hydrogen if n=3.

16. A method according to claim 15 wherein Y and Z each represent hydrogen, and n=2.

17. A method according to claim 16 wherein X represents hydrogen.

18. A method according to claim 15 wherein one only of Y and Z represents a phenyl or substituted phenyl or benzyl or cyclohexyl group.

19. A method according to claim 15 wherein the organic peroxyacid is present in a washing composition containing from 0.5 to 50% w/w of the organic peroxyacid, from 1 to 90% w/w surfactant, from 0 to 90% w/w detergent builder, from 0 to 90% w/w diluent, and from 0 to 20% w/w minor components.

* * * * *